(12) United States Patent
Rinner

(10) Patent No.: US 6,739,068 B1
(45) Date of Patent: May 25, 2004

(54) PLIERS WITH JAW SPACING AND LOAD MEASURING READINGS

(75) Inventor: James A. Rinner, Racine, WI (US)

(73) Assignee: Pilling Weck Incorporated, Horsham, PA (US)

( * ) Notice: Subject to any disclaimer, the term of this patent is extended or adjusted under 35 U.S.C. 154(b) by 0 days.

(21) Appl. No.: 10/336,677

(22) Filed: Jan. 6, 2003

(51) Int. Cl.[7] .............................. G01B 5/02; A61B 17/66
(52) U.S. Cl. ............................................. 33/783; 33/806
(58) Field of Search ........................ 33/783, 784, 792, 33/794, 797, 798, 800, 801, 806, 807, 813, 815, 512, 542; 7/125; 606/57

(56) References Cited

U.S. PATENT DOCUMENTS

| | | |
|---|---|---|
| 466,986 A | 1/1892 | Van Roden |
| 1,528,273 A | 3/1925 | Shwed |
| 1,626,540 A | 4/1927 | Kimura |
| 2,112,873 A | 4/1938 | Wright ............................ 81/18 |
| 2,125,945 A | 8/1938 | Montgomery |
| 2,396,619 A | 3/1946 | Strayer |
| 2,591,360 A | 4/1952 | Keenan ........................... 81/47 |
| 2,888,825 A | 6/1959 | Krafft |
| 3,140,546 A | 7/1964 | Bartlett ......................... 33/148 |
| 3,140,715 A | 7/1964 | Whitton |
| 3,391,573 A | 7/1968 | Hiller |
| 3,559,515 A | 2/1971 | Kyser |
| 3,740,779 A | 6/1973 | Rubricvis ................... 7/14.1 R |
| 4,050,464 A | 9/1977 | Hall |
| 4,127,112 A | 11/1978 | Sherlock et al. ............... 128/25 |
| 4,184,259 A | 1/1980 | Sosnay ........................... 433/4 |
| 4,226,025 A | 10/1980 | Wheeler ........................ 33/148 |
| 4,312,363 A | 1/1982 | Rothfuss et al. ............. 128/774 |
| 4,432,376 A * | 2/1984 | Huszar ........................... 33/784 |
| 4,633,587 A | 1/1987 | Harrison ........................ 30/261 |
| 4,843,721 A | 7/1989 | Hoge ............................. 33/802 |
| 4,898,161 A * | 2/1990 | Grundei ........................ 606/105 |
| 5,070,623 A | 12/1991 | Barnes .......................... 33/807 |
| 5,116,340 A | 5/1992 | Songer et al. ............... 606/103 |
| 5,156,161 A | 10/1992 | Lollar .......................... 128/774 |
| 5,183,055 A | 2/1993 | Seager |
| 5,297,538 A * | 3/1994 | Daniel .......................... 600/206 |
| 5,336,228 A | 8/1994 | Cholhan ....................... 606/119 |
| 5,381,799 A | 1/1995 | Hamilton et al. ............ 128/777 |
| 5,433,015 A * | 7/1995 | Mazenet ........................ 33/815 |
| 5,597,305 A | 1/1997 | Ray |
| 5,658,295 A | 8/1997 | Krementsov ................. 606/119 |
| 6,048,322 A | 4/2000 | Kushida ....................... 600/587 |
| 6,102,909 A * | 8/2000 | Chen et al. .................... 606/45 |
| 6,263,770 B1 | 7/2001 | Gomas et al. ................. 81/427 |
| 6,551,316 B1 * | 4/2003 | Rinner et al. .................. 606/57 |
| 6,553,685 B2 * | 4/2003 | Nishina et al. ................ 33/815 |

* cited by examiner

Primary Examiner—Christopher W. Fulton
(74) Attorney, Agent, or Firm—Arthur J. Hansmann

(57) ABSTRACT

A pliers with two handles and two jaw portions, all pivoted together. Two readable combinations, each having a scale and a pointer, are on the handles to respectively reveal the amount of pivot and the force applied to a workpiece. A parallel linkage assembly can be attached to the jaw portions for contacting the workpiece, and, because of the parallelism, the location of the contact with the workpiece is not critical to the readings.

23 Claims, 4 Drawing Sheets

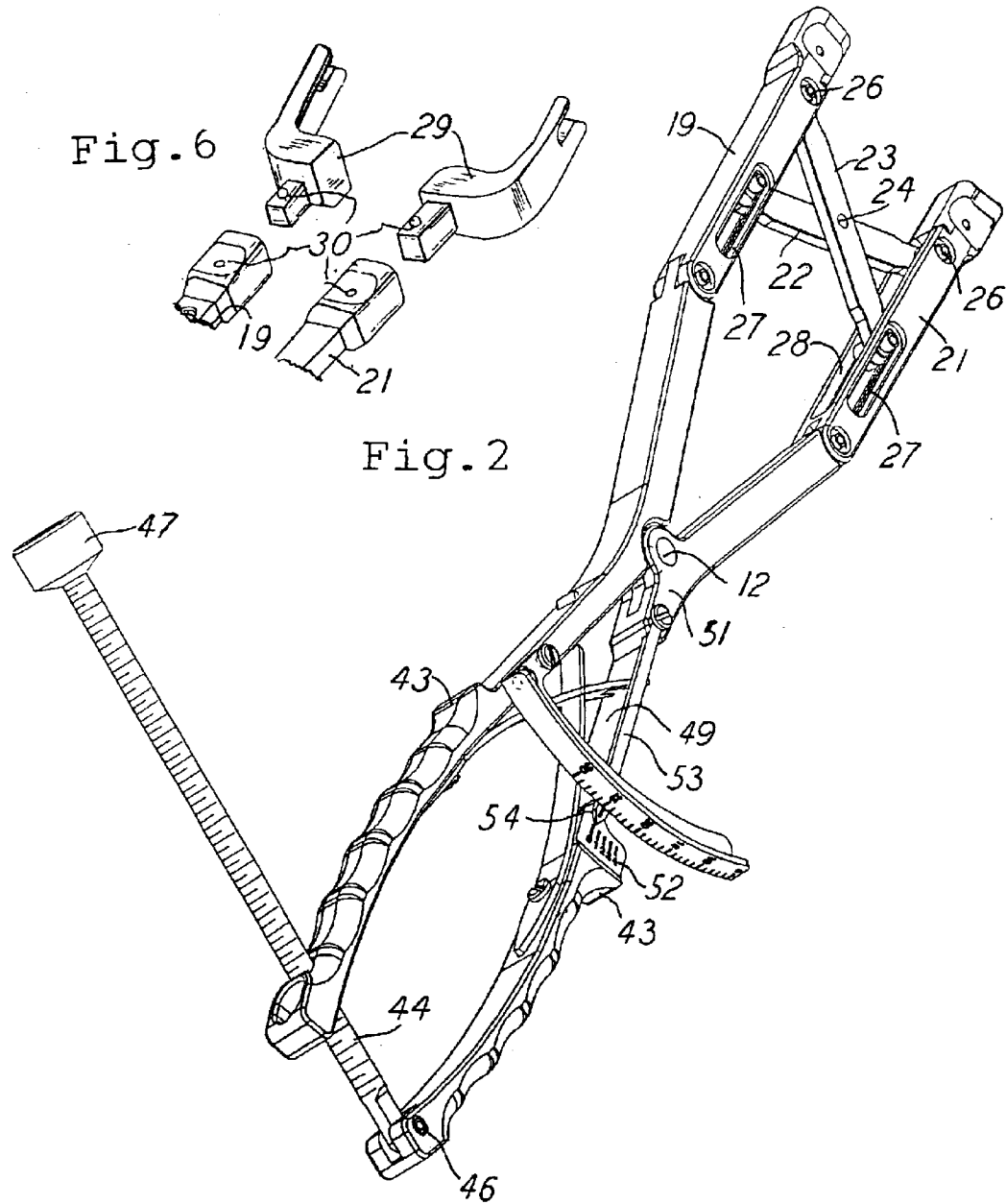

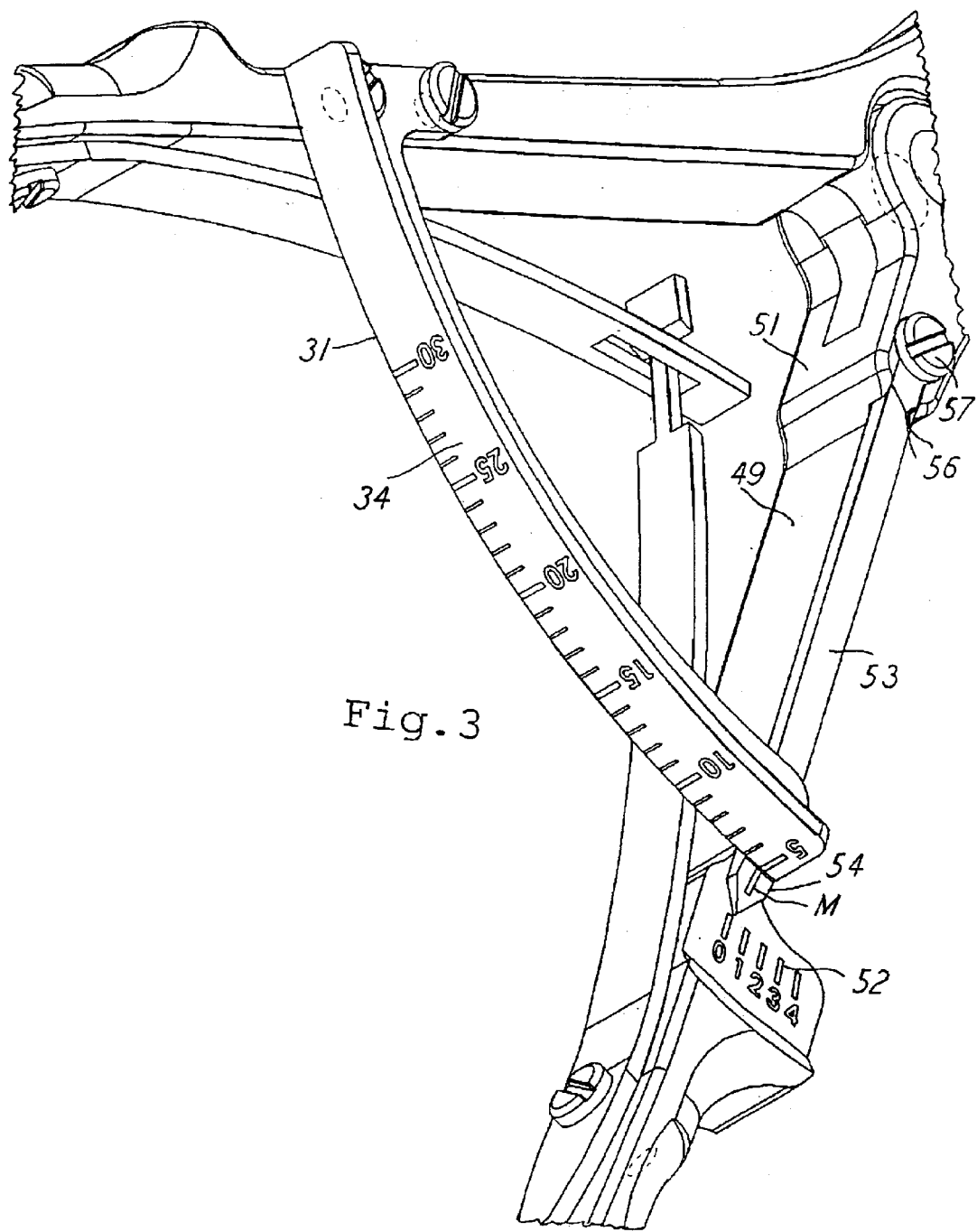

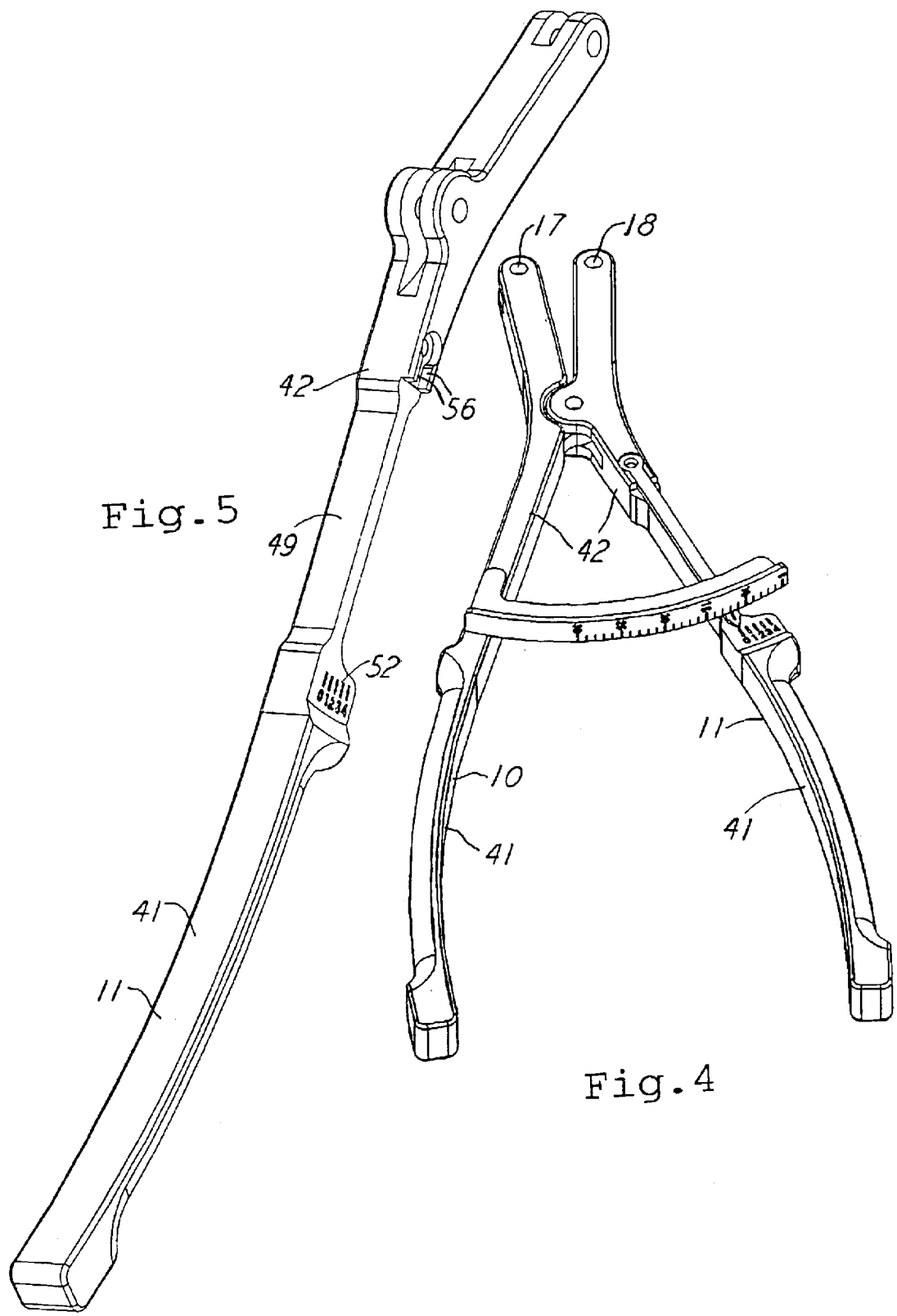

PLIERS WITH JAW SPACING AND LOAD MEASURING READINGS

This invention relates to pliers with jaw spacing and load measuring readings, including a method of applying forces, and, more particularly, it relates to an instrument having jaws for gripping a workpiece and for measuring the gripping distance between the jaws and for measuring the force applied to the workpiece.

BACKGROUND OF THE INVENTION

The prior art is already aware of instruments, like pliers-type instruments with pivotal handles and jaws, for manipulating a workpiece. Those instruments also include means for detecting the amount of pivoting between the handles when the jaws are in contact with the workpiece, and the instruments can detect the distance between the gripping locations on the workpiece. That can be a caliper-type instrument. The prior art also has arrangements of instrument handles which are resilient, or which have a resilient portion or addition, all for applying a force on the jaws through the resilient portion.

The present invention improves upon the prior art by providing an instrument with jaws and pivotal handles wherein the amount of handle pivot, when in contact with the work piece, can be read, and thus the distance between the contacts on the workpiece, and the amount of the forces applied to the workpiece, can be measured. With the detection of the applied forces, only continuous squeezing of the handles is required to produce the application of the desired forces, and this instrument will reveal the amount of those forces at various and selected stage, of force application.

This instrument is capable of applying and measuring various forces and not just one force which is applied by the fixed structural nature of the prior art instruments. In the use of this instrument in medical practice, such as in spine manipulation where force and measurement on vertebrae are required, this instrument will reveal the dimension on the spine and also the forces being applied to the spine. This all occurs with the need of only one gripping position on the handles and with the need of only continuous squeezing or pivoting of those handles.

The indicator, markers, scales, and pointers, whichever are employed, are arranged to be visible, and thus readable, from one viewing location or perspective, so the user need not strain nor move to read all the measurements. The user's grip on the handles need not be released nor even moved from its normal squeezing location on the handles in order to view the readings.

Also, the aforementioned is accomplished with an instrument which can have parallel action jaws and which can be arranged for either compression or distraction action on the workpiece. The distraction can be employed on the spine for moving the vertebrae apart while applying only a specific and accurate distraction force of separation, and while the instrument displays the measurement of the changing distraction forces. With that arrangement, the readings are accurate because the length of the torque arm on each of the jaws is always constant, regardless of the location of the contact of the jaws with the workpiece, and the parallel linkage assembly provides for, and does not alter, that constant torque arm length. That constancy also pertains to the method.

Throughout, the instrument can have a spring for urging the handles apart and against the squeezing forces being applied, and it can have a threaded member for threadedly actuating the handles relative to each other to squeeze the handles for establishing the pivot action of the handles and securing them and the jaws at any selected pivoted position. Further, there is provision for restricting the pointer indicator for aligning it at a zero setting and thereby automatically achieving desired calibration of the instrument before using it.

A parallel linkage assembly is employed to achieve consistent readings by avoiding a torquing action applied to the workpiece by the pivoting handles. That is, the leverage of the pivoting is not effective beyond a set location on the instrument, and that is the location where parallel linkage may be connected in the instrument.

BRIEF DESCRIPTION OF THE DRAWINGS

FIG. 2 is a perspective view similar to FIG. 1 but with the instrument in an operating open position.

FIG. 3 is an enlarged perspective view of a portion of FIG. 1.

FIG. 4 is a perspective view similar to FIG. 1 but with the instrument in an open operating position and with parts removed.

FIG. 5 is an enlarged perspective view of a portion of FIG. 1.

FIG. 6 is a perspective view of a fragment of FIG. 2, with parts added thereto.

DETAILED DESCRIPTION OF A PREFERRED EMBODIMENT AND METHOD

Figure 1:
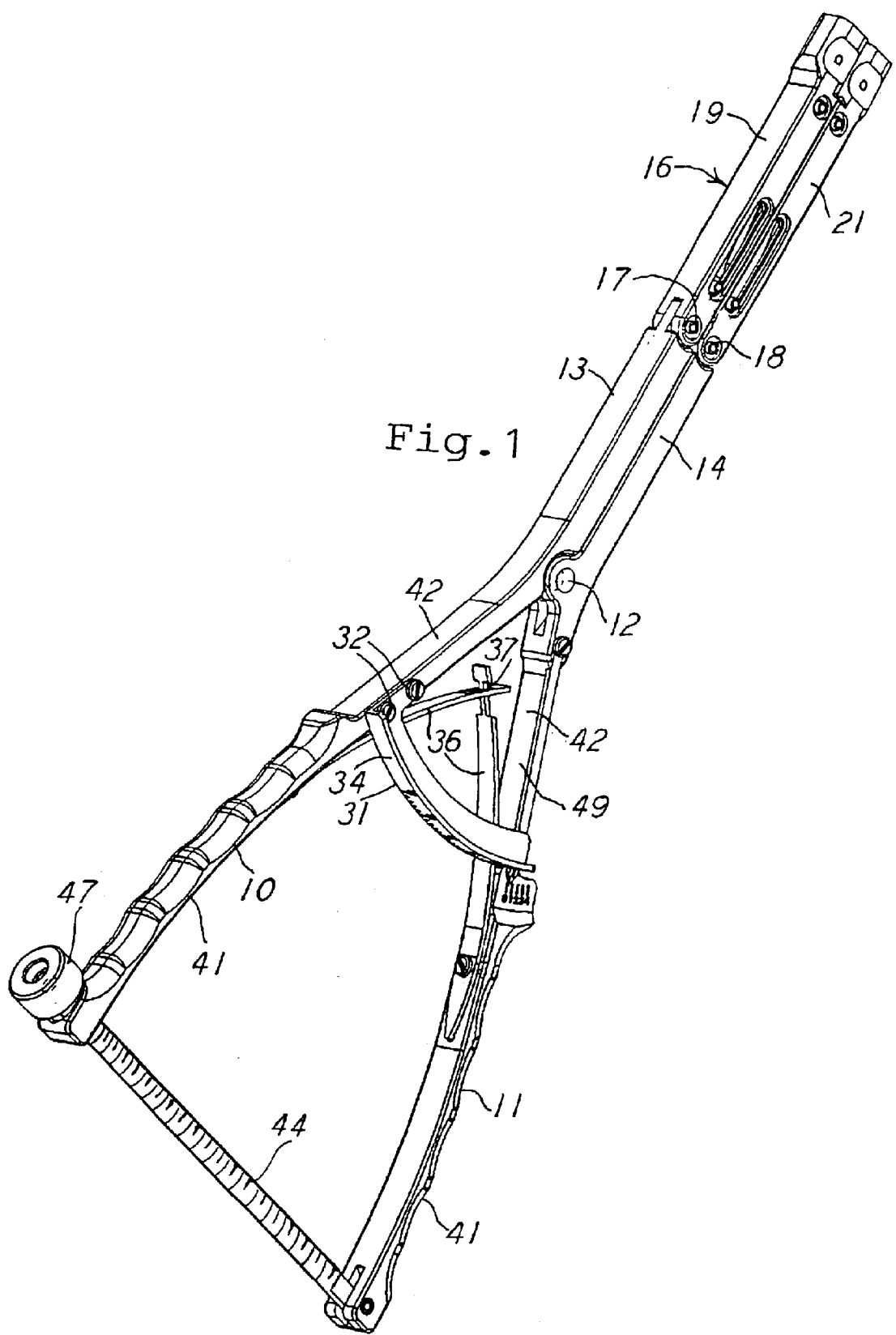
FIG. 1 is a perspective view of an embodiment of this invention.

In the sense that the instrument of this invention is like pliers, it will be mentioned in that term. There are two handles 10 and 11 which are pivoted together by a pivot post 12 extending therebetween. Two jaws 13 and 14 are integral with the handles 10 and 11 and are disposed on the side of the pivot 12 opposite from the handles 10 and 11. At this time it will be noticed that the jaws 13 and 14 do not cross over each other but instead are on the same sides of the pivot as the respective handles 10 and 11. That is, the jaws are arranged for distraction in the embodiment shown herein, but it will be understood that the jaws could be on sides opposite from the respective handles and thus be arranged to compress rather than distract. That is, upon squeezing the handles 10 and 11 to move then toward each other, the jaws 13 and 14 will move away from each other.

Another feature is revealed in the showing of a parallel linkage assembly 16 which is connected with, and is an extension of, the jaws 13 and 14. The jaws proper 13 and 14 have connecting posts 17 and 18, and the assembly 16 is pivotally connected at the posts 17 and 18 through two links 19 and 21. Two other links 22 and 23 pivotally and slidably connect to the links 19 and 21 and are pivoted together at 24. Links 23 and 24 are pivoted to the respective links 19 and 21, such as at 26, and they also are slidably connected to the links 19 and 21, such as at the slots 27, to thereby maintain the links 13 and 14 in parallel relationship to each other throughout all degrees of movement of the jaws 13 and 14 as induced by the pivot action of the handles 10 and 11. The links 19 and 21 each have a recess 28 for full reception of the links 22 and 23 in the closed position, such as in FIG. 1.

It will be understood that the aforementioned arrangement is for distraction, and thus the workpiece, which is not shown but could be vertebrae, can be contacted by blades 29 removably attached to the extending ends of the links 19 and 21. The blades 29 are reversible in their mounting, and they have a snap-in connection at 30 so they can be reversed, and they are shown with an offset finger, such as disclosed in U.S. patent application Ser. No. 09/796,410, filed Mar. 2, 2002, and now U.S. Pat. No. 6,551,316, issued Apr. 22, 2003. Equal and directly opposed forces can be applied to the vertebrae, as desired.

The instrument could also be used without the parallel linkage assembly 16, such as arranged in FIG. 4. Further it could be arranged with the jaws crossing over each other at the pivot 12 so that the jaws move toward each other upon squeezing the handles 10 and 11. As such, it is then a compression instrument akin to the action of pliers.

The arrangement could be as disclosed in the aforesaid cited patent.

JAW SPACING READING

Where the pliers of this invention is arranged to reveal both types of readings, the first reading to appear, in response to squeezing the handles 10 and 11, is the jaw spacing reading. That reading is on the scale 31 which is affixed to the handle 10 by a screws 32 and the scale 31 has an arcuate shape extending over the handle 11 when the instrument is in the maximum opening of the handles, as seen in FIG. 1. As seen in FIG. 3, scale 31 has a face 34 on the convex arcuate extent, and the scale 31 carries indicia, such as the sequential numbers shown to be from "5" to "30". In the handle wide open position, the reading at "5" aligns with a marker M affixed to the handle 11.

Both the scale 31 and the marker M will move in an arc upon initial pivoting of the handles 10 and 11 about the pivot axis 12, thus the indicia on the scale 31 and the marker M will always be contiguous to each other for an accurate reading of the amount of pivot of the handles. That gives information about the amount of the spacing between the jaws 13 and 14. With the jaws closed, as in FIGS. 1 and 3, the reading will be on the indicia "5" to reveal that the jaws are indeed closed in contact with each other and there is no space between the jaws 13 and 14. Utilizing "5" etc. for the indicia is arbitrary and different indicia could be used, but scale graduation is significant to show the relative amount of jaw spacing.

At this point of operation, the marker M will pivotally move with the pivotal movement of the handle 11. Later in this description and later in handle movement, it will be seen to be different from that.

Two springs 36 are respectively anchored on the handles 10 and 11, and they contact each other at 37. The springs 36 therefore yielding urge the handles 10 and 11 away from each other, and to the jaw-closed position. The force of the springs 36 is overcome by the user squeezing the handles 10 and 11 toward each other to open the jaws, as desired. Different spring openers could be substituted.

The jaw spacing can be used to reveal the amount of space between two workpieces, or parts thereof, such as workpieces which might be in contact with the blades 29 in the distraction mode of the pliers, which is the mode shown herein. As such, the pliers can be used on the workpiece in the nature of a caliper to measure a distance on the workpiece. The higher the aligned reading on the scale by the marker M the greater the spacing between the jaws.

The handles 10 and 11 have grip portions 41 along the lengths thereof which are rearward and approximately one-half the total length of the handles 10 and 11, as best seen in the modified form in FIG. 4. The scale 31 and marker M are approximately at the intersection of the handle halves which are 41 and 42. The grips 41 have an abutment 43 which blocks the user's hand from obscuring the user's view of the scale 31 and marker M when the hand is gripping the grips 41. The handles are of rigid material, except as described later, so they can pivot in response to being squeezed together and forced apart by springs 36.

Another way of pivoting the handles 10 and 11 together, and then holding them at that pivoted position, is with a threaded rod 44 which is pivotally attached to the handle 11 at pin 46 and the rod 44 extends through handle 10, such as seen in FIG. 2. A knob 47 is threaded onto the rod 44 and the knob 47 can be positioned to abut the handle 10 and thereby secure the spacing of the handles 10 and 11 relative to each other and against the force of the springs 36 which urge the handles apart. Also, the knob 47 and rod 44 can be employed to threadedly move the knob along the rod and thereby force on the handles 10 and 11 to create the handle pivoting, as desired.

LOAD MEASURING READING

When the jaws 19 and 21, having thereon any attachments for contacting a workpiece, such as attachments 29 and such as in the cited patent above, engage the workpiece, they basically have no further movement. That is, they abut the workpiece, and that can be when the pliers is arranged for either mode of compression or distraction, per the cited patent and the description herein. In either mode, the handles will always be squeezed together to apply the force on the workpiece, and the jaws 19 and 21 will move either toward or away from each other.

When the jaws 19 and 21 become immobile because of workpiece contact, further squeezing of the hand grips 41 will be measured in the amount of force being applied on the workpiece. To achieve that measuring, the handle 11 is constructed to have a resilient length for its inner portion or approximate half the length of the handle 11 as seen at 49. The handle 11 has a rigid length 51 extending from the pivot 12, and that length 51 is connected with the resilient length 49 which is connected with the grip 41 of the handle 11. Thus, the handle 11 is continuous from its extent from the pivot 12 to the pivot 46, but the length 49 is resilient.

There is a scale 52 on the handle 11, and it happens to carry the indicia designated from "0" to "4", though other numbers could be used, the graduation of those numbers is all that is important. That scale is affixed to the handle 11 adjacent the abutment 43, and it pivots along with the pivoting of the handle 11. The portion 49 can be of a spring steel material, or any other material that provides the resilience desired herein. The length 49 is sufficiently firm to pivot with the pivoting handle 11 until resistance is presented by the workpiece. Therefore, there is an accurate showing on the scale 52 of the amount of pivot of the handles relative to workpiece contact, and that amount of pivot is shown on the scale 31.

Beyond that stage of contact, the workpiece will present a resistance to further movement of jaw 16 and that is when further squeezing on the handles 10 and 11 will cause the resilient portion to flex in proportion to the force being applied by squeezing or threadedly forcing on the handles, and that flexing is in accord with the force applied to the workpiece. At that time, the workpiece may either move or remain in position of initial contact, depending on its own sturdiness.

An elongated pointer 53 is attached to the handle rigid portion 51 and extends to the scale 52 where it terminates in an arrowhead 54. The pointer 53 always extends in only one direction of from the portion 51 in that it always retains its pointing direction off portion 51 as shown in the drawings, it does not deviate from that shown pointed direction relative to portion 51. FIG. 3 shows that the pointer 53 is nested in a recess defined by two spaced-apart shoulders 56, so the pointer 53 cannot pivot or otherwise move relative to the handle portion 51. A screw 57 holds the pointer down into the recess defined by the two shoulders 56.

The marker M is on the extending end or arrowhead 54 of the pointer 53, so it too remains in its shown and set position throughout the operation of this instrument.

When the handles are forced against the workpiece beyond that initial point of workpiece contact, the material 49 can flex to move the scale 52 relative to the stationary pointer 54. That is, the scale 52 will show the measurement of the flexing force, per the indicia "0" to "4" to reveal to the user the amount of force that is being applied to the workpiece. In the shown embodiment, the handle 11 has the scale 52 and the pointer 53, along with a resilience that allows bending of the handle, to reveal a reading regarding the force being applied to the workpiece. Under additional force, the handle 11 bends from the position shown in the drawings. Upon release of the pivoting force, the handle returns to the position shown, which is a zero position. Throughout, the pointer always remains set in its shown position. While there is leverage force on both the handles 10 and 11 and consequently on the jaws 13 and 14 at the locations 17 and 18, with the parallel linkage assembly 16, there will always be a consistent reading of the force on the workpiece because that force is determined at 17 and 18, the extent of the application of the leverage about the pivot 12. So, even the location of the contact of the instrument on the workpiece, such as along blades 29, will not alter an accurate reading of the applied force.

One application of this instrument could be where the workpiece has two separated portions, such as with vertebrae, and the distraction mode will detect the spacing between the two adjacent vertebrae, on the scale 31, and then it will also detect the amount of force applied when the handles are pivoted until the resilient portion 49 becomes active, as shown on the scale 52.

The description of the method of this invention is inherent in the foregoing description and is therefore disclosed herein.

It will be obvious to one skilled in the art that changes could be made from that which is described and shown herein. There could be only either the jaw spacing arrangement, or only the load measuring arrangement. The arrangement for the jaw spacing reading has the resilient length 49. The complete arrangement will be with the combined two features.

What is claimed is:

1. Pliers with jaw spacing and load measuring readings, comprising:

two jaws movable toward and away relative to each other, a first handle and a second handle pivoted together and operative on said jaws for moving said jaws in response to force on said handles for pivoting said handles, a graduated scale on said first handle for movement therewith and extending to said second handle, a marker on said second handle adjacent said graduated scale for revealing a pivoted relationship between said handles and thus reveal a spacing between said jaws, a resilient portion included in said second handle for movement of said second handle relative to said first handle and in addition to the aforementioned pivoting of said handles and in response to force on said second handle and thereby on said jaws, and a combination of a scale and pointer on said second handle for measuring the additional movement.

2. The pliers with jaw spacing and load measuring readings, as claimed in claim 1, including:

said scales being disposed offset from each other whereby said scales and said marker and said pointer can all be simultaneously viewed while the pliers remain in one position.

3. Pliers with jaw spacing and load measuring readings, comprising:

two jaws movable toward and away relative to each other, a first handle and a second handle pivoted together and operative on said jaws for moving said jaws, a graduated scale on said first handle for movement therewith and extending to said second handle, a marker on said second handle adjacent said graduated scale for revealing a pivoted relationship between said handles and thus reveal a spacing between said jaws, a resilient portion included in one of said handles for movement of said one of said handles in addition to the pivoting of said handles and in response to force on said handles and thereby on said jaws, and a combination of a scale and pointer on said one of said handles for measuring the additional movement.

4. The pliers with jaw spacing and load measuring readings, as claimed in claim 3, including:

said scales being disposed offset from each other whereby said scales and said marker and said pointer can all be simultaneously viewed from the handle end of the pliers from one viewing perspective.

5. The pliers with jaw spacing and load measuring readings, as claimed in claim 3, wherein:

said one of said handles has a length and said resilient portion extends along said length and has a first end connected adjacent said jaws and a second end distal from said first end, for flexing said resilient portion in response to forces on said handles, and said pointer is anchored adjacent said first end and extends to adjacent said second end where said pointer is free to remain in position upon flexing said resilient portion.

6. The pliers with jaw spacing and load measuring readings, as claimed in claim 3, including:

a threaded member connected between said handles for threadedly controlling the movement between said handles.

7. The pliers with jaw spacing and load measuring readings, as claimed in claim 3, including:

said jaws being in a parallel linkage assembly on said handles for parallel movement of said jaws relative to each other and in response to pivoting of said handles.

8. Pliers with load measuring readings, comprising:

two jaws movable toward and away relative to each other, a first handle and a second handle pivoted together for initial movement therebetween and being operative on said jaws for movement of said jaws, a resilient portion included in one of said handles for movement of said one of said handles in addition to the initial movement and in response to force on said handles and thereby on said jaws, and a scale and pointer combination on said one of said handles for measuring the additional movement.

9. The pliers with load measuring readings, as claimed in claim 8, wherein:
there is a marker on one of said handles and is disposed relative to the scale of said combination and the pointer of said combination is restrictively guided on said one of said handles and is thereby aligned relative to said marker.

10. The pliers with load measuring readings, as claimed in claim 8, including:
a threaded member connected between said handles for threadedly controlling the movement between said handles.

11. The pliers with load measuring readings, as claimed in claim 8, including:
said jaws being in a parallel linkage assembly on said handles for parallel movement of said jaws relative to each other and in response to the movement of said handles.

12. The pliers with load measuring readings, as claimed in claim 8, including:
an additional pointer and scale operative between said handles for revealing the amount of movement between said handles.

13. Pliers with load measuring readings, comprising:
two jaws movable toward and away relative to each other,
a first handle and a second handle connected for pivotal movement and being operative on said jaws for movement of said jaws,
one of said handles having a first length rigidly connected with one of said jaws and having a second length extending beyond said first length and being of resilient material for moving relative to said first length beyond said pivotal movement and doing so in response to force on said one of said handles,
a pointer on said first length and extending beyond said second length to a distal end of said pointer, and
a scale on said one of said handles adjacent said pointer distal end for measuring the force transmitted through said resilient material.

14. The pliers with load measuring readings, as claimed in claim 13, wherein:
said pointer is restrictively mounted on said one of said handles at said first length thereof for restrictive alignment with said scale and said pointer is of a length equal to the length of said resilient member.

15. Pliers with load measuring readings, comprising:
two jaws movable toward and away relative to each other,
handles pivoted together for initial relative movement therebetween and being operative on said jaws for movement of said jaws into contact with a workpiece,
said handles being capable of additional relative movement while in contact with said workpiece, and
an indicator on said handles for measuring the additional movement.

16. The pliers with load measuring readings, as claimed in claim 15, wherein:
said indicator includes a pointer on one of said handles and a scale on the other of said handles and said pointer and said scale are restrictively mounted for alignment therebetween for zero setting thereof.

17. The pliers with load measuring readings, as claimed in claim 15, including:
a threaded member connected between said handles for threadedly controlling the movement between said handles.

18. The pliers with load measuring readings, as claimed in claim 15, including:
said jaws being in a parallel linkage assembly on said handles for parallel movement of said jaws relative to each other and in response to the movement of said handles.

19. The pliers with load measuring readings, as claimed in claim 18, including:
flat blades on said assembly for engaging the workpiece.

20. The pliers with load measuring readings, as claimed in claim 15, including:
a pointer and scale operative between said handles and in addition to said indicator for revealing the amount of movement between said handles.

21. A method of making load measuring readings on a workpiece and with a pliers instrument which has an pivoted assembly of two handles and two jaws pivoted together at a pivot point and with both said handles and both said jaw extending away from said pivot point, comprising the steps of:
articularly connecting a linkage assembly of a plurality of links to said jaws to extend from said jaws and away from said pivot point and with two of said links being parallel to each other and each having a first end pivotally connected to said jaws and each having a portion extending away from said first end,
contacting the workpiece with said portions at any location along the extent of said portions,
pivoting said jaws and thereby moving said two links relative to each other while retaining the parallel relationship between said links and thereby produce only one amount of force on the workpiece regardless of the location of the contact by said portions on the workpiece, and thereby circumventing the torquing action otherwise inherent in the pivoting of said jaws, and
providing a scale and pointer on said handles and reading the indication on the scale and pointer to thereby determine the amount of force being applied when said jaws contact the workpiece.

22. The method of making load measuring readings on a workpiece, as claimed in claim 21, including the step of:
causing said handles to flex under the force on said workpiece and moving said pointer in response to the amount of flexing and reading the total amount of force indicated by said pointer on said scale.

23. The method of making readings on a workpiece, as claimed in claim 21, including the step of:
actuating a scale and marker on said handles and reading the spacing between said jaws when said jaws are in contact with the workpiece.

* * * * *